United States Patent
Pankratz et al.

(10) Patent No.: US 10,105,205 B2
(45) Date of Patent: Oct. 23, 2018

(54) MUSCLE WALL DEFECT PROSTHESIS AND DEPLOYMENT SYSTEM

(71) Applicant: Bard Shannon Limited

(72) Inventors: Stephen Werner Pankratz, Oakville (CA); Lahav Gil, Toronto (CA)

(73) Assignee: Bard Shannon Limited, Humacao, PR (US)

( * ) Notice: Subject to any disclaimer, the term of this patent is extended or adjusted under 35 U.S.C. 154(b) by 329 days.

(21) Appl. No.: 14/956,598

(22) Filed: Dec. 2, 2015

(65) Prior Publication Data
US 2016/0151139 A1    Jun. 2, 2016

Related U.S. Application Data

(60) Provisional application No. 62/086,371, filed on Dec. 2, 2014.

(51) Int. Cl.
*A61F 2/02*    (2006.01)
*A61F 2/00*    (2006.01)

(52) U.S. Cl.
CPC ...... *A61F 2/0063* (2013.01); *A61F 2002/009* (2013.01); *A61F 2002/0072* (2013.01)

(58) Field of Classification Search
CPC ............ A61F 2/0063; A61F 2002/0072; A61F 2002/009
USPC ....................................... 606/151; 623/23.72
See application file for complete search history.

(56) References Cited

U.S. PATENT DOCUMENTS

| | | |
|---|---|---|
| 5,258,000 A | 11/1993 | Gianturco |
| 5,366,460 A | 11/1994 | Eberbach |
| 5,370,650 A | 12/1994 | Tovey et al. |
| 5,425,740 A | 6/1995 | Hutchinson, Jr. |
| 5,634,931 A | 6/1997 | Kugel |
| 5,769,864 A | 6/1998 | Kugel |
| 5,916,225 A | 6/1999 | Kugel |
| 6,132,470 A | 10/2000 | Berman |
| 6,171,318 B1 | 1/2001 | Kugel et al. |
| 6,174,320 B1 | 1/2001 | Kugel et al. |

(Continued)

FOREIGN PATENT DOCUMENTS

| | | |
|---|---|---|
| EP | 1336391 A1 | 8/2003 |
| EP | 1336391 B1 | 12/2011 |

(Continued)

OTHER PUBLICATIONS

International Preliminary Report on Patentability for International Application No. PCT/US2015/063386, dated Jun. 15, 2017, 9 pages.

(Continued)

*Primary Examiner* — Kathleen Holwerda
(74) *Attorney, Agent, or Firm* — Wolf, Greenfield & Sacks, P.C.

(57) ABSTRACT

A delivery device and implantable prosthesis for repairing a soft tissue defect such as an abdominal wall hernia. The delivery device includes a support body that is nested between a first and second layer of the prosthesis. The support body includes a zone of weakness to facilitate collapse of the nested delivery device and prosthesis. A handle extends from the support body and may be used to position the prosthesis as well as to cause the support body to move to a reduced configuration for removal of the support body from the prosthesis.

29 Claims, 9 Drawing Sheets

(56) References Cited

U.S. PATENT DOCUMENTS

| | | |
|---|---|---|
| 6,290,705 B1 | 9/2001 | Chan et al. |
| 6,290,708 B1 | 9/2001 | Kugel et al. |
| 6,551,356 B2 | 4/2003 | Rousseau |
| 6,575,988 B2 | 6/2003 | Rousseau |
| 6,669,735 B1 | 12/2003 | Pelissier |
| 6,790,213 B2 | 9/2004 | Cherok et al. |
| 6,800,082 B2 | 10/2004 | Rousseau |
| 6,814,743 B2 | 11/2004 | Chin et al. |
| 7,101,381 B2 | 9/2006 | Ford et al. |
| 7,544,203 B2 | 6/2009 | Chin et al. |
| 7,785,334 B2 | 8/2010 | Ford et al. |
| 7,824,420 B2 | 11/2010 | Eldridge et al. |
| 7,947,062 B2 | 5/2011 | Chin et al. |
| 7,963,942 B2 | 6/2011 | Chen |
| 8,753,358 B2 | 6/2014 | Cook |
| 8,808,315 B2 | 8/2014 | Bailly et al. |
| 8,920,370 B2 | 12/2014 | Sholev et al. |
| 8,945,235 B2 | 2/2015 | Horton et al. |
| 9,005,223 B2 | 4/2015 | Cardinale et al. |
| 2001/0016754 A1 | 8/2001 | Adams et al. |
| 2002/0013590 A1 | 1/2002 | Therin et al. |
| 2004/0019360 A1 | 1/2004 | Farnsworth et al. |
| 2004/0073257 A1 | 4/2004 | Spitz |
| 2004/0087980 A1 | 5/2004 | Ford et al. |
| 2005/0043716 A1 | 2/2005 | Frimer |
| 2007/0299538 A1 | 12/2007 | Roeber |
| 2008/0147200 A1 | 6/2008 | Rousseau et al. |
| 2008/0237287 A1 | 10/2008 | Mitchinson |
| 2009/0082792 A1 | 3/2009 | Koyfman et al. |
| 2009/0270999 A1 | 10/2009 | Brown |
| 2009/0326676 A1 | 12/2009 | Dupic et al. |
| 2010/0069930 A1 | 3/2010 | Roslin et al. |
| 2010/0241145 A1 | 9/2010 | Cook |
| 2011/0040311 A1 | 2/2011 | Levin et al. |
| 2011/0054500 A1 | 3/2011 | Levin et al. |
| 2011/0082479 A1 | 4/2011 | Friedlander |
| 2011/0144667 A1 | 6/2011 | Horton et al. |
| 2011/0224704 A1 | 9/2011 | Bailly et al. |
| 2011/0295283 A1 | 12/2011 | Darois et al. |
| 2013/0103058 A1* | 4/2013 | Gobran ............... A61F 2/0063 606/151 |
| 2013/0178876 A1 | 7/2013 | Horton et al. |
| 2013/0317527 A1 | 11/2013 | Jacinto et al. |
| 2014/0025093 A1* | 1/2014 | Horton ............... A61F 2/0063 606/151 |
| 2014/0051915 A1 | 2/2014 | Sholev et al. |
| 2014/0088619 A1 | 3/2014 | Ethicon |
| 2014/0316444 A1 | 10/2014 | Pankratz |
| 2015/0148824 A1 | 5/2015 | Horton et al. |
| 2015/0257866 A1 | 9/2015 | Filipiak et al. |

FOREIGN PATENT DOCUMENTS

| | | |
|---|---|---|
| EP | 2543339 A1 | 1/2013 |
| JP | 2009-541011 T | 11/2009 |
| WO | WO 2009/097380 A1 | 8/2009 |
| WO | WO 2011/043795 A1 | 4/2011 |
| WO | WO 2011/128903 A2 | 10/2011 |
| WO | WO 2013/148839 A1 | 10/2013 |
| WO | WO 2014/117270 A1 | 8/2014 |
| WO | WO 2015/104014 A1 | 7/2016 |

OTHER PUBLICATIONS

Vanos, Robilyn; International Search Report from corresponding PCT Application No. PCT/CA2014/050057; search dated Apr. 29, 2014.

International Preliminary Report on Patentability for Application No. PCT/CA2014/050057 dated Aug. 4, 2015.

International Search Report and Written Opinion for Application No. PCT/US2015/063386 dated Mar. 18, 2016.

Extended European Search Report for Application No. 14746593.4 dated Jul. 12, 2016.

\* cited by examiner

MUSCLE WALL DEFECT PROSTHESIS AND DEPLOYMENT SYSTEM

RELATED APPLICATIONS

This Application claims priority under 35 U.S.C. § 119(e) to U.S. Provisional Application Ser. No. 62/086,371, entitled "MUSCLE WALL DEFECT PROSTHESIS AND DEPLOYMENT SYSTEM" filed on Dec. 2, 2014, which is herein incorporated by reference in its entirety.

FIELD OF THE INVENTION

This invention relates to apparatus and a method for facilitating the repair of hernias and muscle wall defects. It relates more particularly to a system that aids in the positioning and fixation of a prosthesis over the muscle wall defect.

BACKGROUND OF THE INVENTION

One method of repairing a muscle wall defect or hernia of a patient's abdominal wall muscle is to insert a prosthetic material or mesh through the defect and so as to be inside the patient's muscle wall. The prosthesis, which is generally larger than the defect, is then positioned in a planar orientation relative to the muscle wall, covering the defect in its entirety. The prosthesis is then typically fixed to the underside of the muscle wall or tissue surrounding the defect, with the use of fixation tools such as sutures and/or tackers.

A second method of repairing a hernia is to place the prosthetic material or mesh through the muscle wall defect, and position it in a planar orientation between the muscle wall and the posterior sheath.

Prosthetic devices have recently been developed that aid in the orientation, positioning and fixation of the prosthesis to the underside of the muscle wall defect. These devices generally consist of (a) a prosthesis or base that may be folded and placed through the defect; (b) a support member or washer that is combined with the prosthesis and that urges the prostheses into a planar orientation after it has been placed through the defect; and (c) a handle or positioning straps that can extend through the defect and can be used to hold the prostheses close to or against the muscle wall while the prosthesis is sutured or tacked to the abdominal wall. At least a portion of positioning straps are subsequently cut off once the prosthesis is fixed in place, allowing tissue anterior to prosthesis and muscle wall to be sutured closed.

U.S. Pat. No. 7,101,381 describes a prosthesis comprising a resilient support member disposed on a patch, the resilient support member being constructed and arranged to urge the patch into a planar configuration. This additional support member, attached to the layers of the prosthesis, however, is permanently implanted in the patient and introduces additional stiffness or rigidity, which may interfere with the prosthetic's ability to conform to the contours of the patient's abdominal wall. This arrangement makes it more difficult to ensure that the patch remains flat against patients' moving and contoured abdominal wall. The flat and tight junction between the patch and the patients' abdominal wall is necessary for ensuring that intra-abdominal tissue or bowels cannot become wedged between the prosthetic and the abdominal wall, causing a hernia recurrence (particularly for the first method of repairing a hernia described above).

US patent US2011/0144667 attempts to resolve the high degree of stiffness that results from this support member by describing a support washer that is not attached or sutured to the base of the prosthetic, but is instead free-floating. This washer of this device is still, however, contained within the enclosed layers of the prosthesis, and permanently implanted with the prosthesis. While this prosthesis may reduce some of the stiffness when compared to the support member described in U.S. Pat. No. 7,101,381, the reduced stiffness also compromises the ability of the support washer to urge the prosthesis into a planar configuration. Because surgeons must ensure that this prosthesis is in a planar configuration and the prosthesis completely covers the muscle wall defect, many find this device difficult to use.

Both the additional support member described in U.S. Pat. No. 7,101,381, and the free-floating support washer described in US2011/0144667 introduce additional foreign body material that is implanted into the patient. This additional foreign body material not only itself adds rigidity to the abdominal wall, it further compromises the flexibility and physiological function of the abdominal wall by eliciting a foreign body response that results in a stiffer and weaker muscle repair around the prosthetic.

One familiar with the art will recognize the importance of fixing the patch, particularly the peripheral edge of the patch, to the abdominal wall. This facilitates a tight junction between the patch and the muscle wall, and facilitates integration of the patch to the abdominal wall over time. Underlying tissue or organs cannot then become wedged between the patch and the abdominal wall, which could otherwise lead to an incomplete repair, a hernia recurrence, or other post-operative complications.

U.S. Pat. No. 7,101,381 goes on to describe a patch that has an access opening that is adapted to provide entry into the interior of the pocket (between the layers) to facilitate the positioning of the patch over the tissue or muscle wall defect. This pocket may also be accessed by sutures or a tacker in order to fix the patch to the abdominal wall. However, once the patch has been positioned relatively deeply within the abdominal wall, it is difficult or even impossible for a surgeon to see the access opening of the patch during fixation. It is thus very challenging for the surgeon to place instrumentation through the muscle wall defect (which is typically smaller than the patch), into the access opening of the patch, and fix the peripheral edge of the patch to the underside of the abdominal wall, without unintentionally perforating the patient's organs, tissue or other critical structures.

The resilient support member that U.S. Pat. No. 7,101,381 describes and that urges the patch in the planar configuration is disposed on the patch. This support member, and the stitching that disposes the resilient member onto the patch, become the perimeter of the access opening, and a barrier that prevents access through the access opening or pocket, to the peripheral portion or edge of the patch. It is therefore not possible to suture or tack the peripheral portion of the patch to the abdominal wall from within the access opening of the patch. This can prevent complete integration of the patch to the abdominal wall, and can allow patient tissue or organs to be wedged between the patch and the abdominal wall.

In application published as 2014/117270, to Stephen Pankratz, the contents of which are incorporated herein, there is described a prosthesis and placement device which is configured to facilitate insertion, positioning and removal of the support. The placement device includes a support that is insertable in to the prosthesis and has a handle attached to the support. The handle is provided with sufficient stiffness to impart a bending moment to the support. The support has a generally planar surface with a zone of weakness that facilitates movement of the support between a deployed position, in which the prosthesis is supported and a collapsed position for insertion in to and removal from the prosthesis. Proper support for the prosthesis enables the surgeon to insert sutures or staples to secure the prosthesis and mitigates the risk of the suture being misdirected. The zone of weakness in combination with the stiffness of the handle enables the support to be collapsed once the prosthesis is properly secured.

The forces required to collapse and extract the support should be minimized to avoid damage to the tissue surrounding the incision in the abdominal wall as the support is removed. The device shown in US patent publication 2014/117270 maintains the forces required for removal at acceptable levels but in certain circumstances a further reduction is desirable.

It is an object of the present invention to provide a support device for a prosthesis which seeks to attain a further reduction in such forces.

SUMMARY OF THE INVENTION

The present invention relates to a device and method for implanting a prosthesis used to overlie a hernia or abdominal wall defect, and that aids in the orientation, positioning and fixation of the prosthesis to the abdominal wall, while limiting the amount of foreign body material implanted in the patient.

The hernia or soft tissue or muscle repair device and methods described here utilize a system comprising, in combination, a biologically compatible implantable prosthesis or patch, and a delivery device for delivering the prosthesis to the repair site. The biologically compatible implantable prosthesis or patch is comprised of a first layer of material that covers the muscle wall defect. A second layer or rim of material is attached to the first layer at the peripheral edges of each layer, and provides an opening in the form of a hole or slit that allows access to an inner space or pocket formed between the first and second layers.

Both layers of the prosthesis must be comprised of biocompatible material(s), flexible enough to conform to patients' abdominal wan, and must cover patients' muscle wall defect. Synthetic materials may be used, and are intended to provide permanent coverage of the muscle wall defect and reinforcement to prevent future hernia recurrences. These materials include, but are not limited to, polypropylene, polyethylene, polyethylene terephthalate and/or expanded polytetrafluoroethylene, and may be knitted or woven together, and arranged in flexible planar sheets. Examples of such materials include Atrium Medical's Pro-Lite and ProLite Ultra polypropylene hernia mesh, Ethicon's Prolene polypropylene hernia mesh, Bard's Marlex polypropylene hernia mesh and Ethicon's Mersilene mesh constructed from polyethylene terephthalate. These synthetic materials may also be co-knitted with bioabsorbable materials such as polyglycolic acid. The synthetic or synthetic-bioabsorbable knitted material may also be coated on the side that will face the viscera, with a material or combinations of materials that reduce or prevents the adhesions of bowels or other tissue. Examples of these materials include, but are not limited to cross-linked omega-3 fatty acid oil; combinations of sodium hyaluronate, carboxymethylcellulose and polyethylene glycol; oxidized regenerated cellulose; collagen oxidized films; and combinations of monocryl and polydioxanone film. Currently available devices that aid in the positioning and fixation of a prosthesis over the muscle wall defect, and that utilized a prosthesis constructed from combinations of polypropylene and bioabsorbable coatings include Atrium Medical's VPatch™ (which utilizes cross-linked omega-3 fatty acid oil coated polypropylene) and C.R. Bard's Ventrelex ST (which utilizes a combination of sodium hyaluronate, carboxymethylcellulose and polyethylene glycol; and polypropylene).

Alternatively, the prosthesis can be comprised of a collagen matrix, sourced from human tissue (allografts), or animal tissue (xenografts). These materials provide a collagen framework that may be repopulated with the patient's own cells and tissue after implantation and overtime. These sources are typically used when synthetic sources are not recommended, and often used during the repair of infected or contaminated hernia defects. Examples of currently available collagen matrix materials include TEI Biosicence's SurgiMend which is a xenograft sourced from fetal bovine, LifeCell's Alloderm allograft sourced from human cadavers, and LifeCell's Strattice xenograft sourced from porcine.

For delivering the prosthesis, there is also provided a separate delivery device, which is comprised of a flexible and planar support piece, and a handle. The support piece is comprised of a material with elastic and/or flexible properties, that will fold or temporarily collapse from its free body planar configuration. Before use, the support piece of the delivery device is placed or "nested" within the pocket between two layers of the prosthesis. Once positioned in the pocket, the support piece may be released, allowing it to expand back into its natural planar orientation between the two layers of the prosthesis. The support piece of the delivery device is constructed from a material with an inherent rigidity that provides a bias toward a flat or planar orientation yet is sufficiently pliable to allow its deformation during placement at the repair site. Useful materials include, but are not limited to polymeric material such as polypropylene, polyethylene terephthalate, polyethylene, silicone, nitinol and/or polytetrafluoroethylene.

The handle of the delivery device can be in the form of a tether, strap or extension, and may be used to aid in the positioning of the support piece while it is nested in the prosthesis. Because the handle is not attached to the prosthesis, but rather attached to or contiguous with the support piece, the handle may also to be used to remove the removable piece from the prosthesis and out of the defect after the prosthesis has been fixed in place. The handle is constructed of a flexible material that is long enough to extend though the muscle wall defect and surrounding tissue, while being held or handled outside of the defect by the surgeon. It must also be durable enough to withstand the force exerted on it by the surgeon while pulling on it and positioning the removable piece relative to the defect, or removing the removable piece from the prosthesis and out of the muscle wall defect. Some examples of materials that the handle may be constructed from include, but are not limited to polypropylene, polyethylene terephthalate and/or polytetrafluoroethylene.

When the support piece is nested in the prosthesis, the two pieces can then be folded or collapsed as one piece while placed through the muscle wall defect. Once placed through the defect, the delivery device can be allowed to return to its natural, planar shape. This urges the prosthesis, constructed from a material that is typically flexible or flimsy, into a planar orientation relative to the abdominal wall. The handle that is fixed to, or contiguous with the support piece, can be then be used to position the prosthesis relative to the defect. The prosthesis can then be fixed to the abdominal wall muscle or tissue surrounding the defect by using, as an example, sutures and/or a tacker. The support piece of the delivery device is constructed preferably from a material that is difficult to penetrate with fixation tools, and may be used to prevent the suture needles or tacks from unintentionally penetrating underlying organs or tissue during fixation of the prosthesis to the abdominal wall. Then, the support piece can be forced to fold or collapse, and retracted and removed from the prosthesis (or base) through the muscle wall defect by pulling on the removable portion of the delivery device, or on the available handle. This allows for a convenient repair of the muscle wall defect while leaving only the prosthesis implanted. Because no support members or washers are left behind, the prosthesis can better conform to the moving contours of the patient's abdominal wall. There is also less foreign body material implanted in the patient, leading to a better, more flexible muscle wall defect repair.

In one embodiment, the space or pocket created between the first layer and second layer or rim of the prosthesis may be accessed so that the second layer that extends about the rim of the first piece may be positioned and fixed to the muscle wall. This pocket is not interrupted by any support member, washer, or stitching that disposes a support member or washer onto the patch. Thus, the pocket may extend all the way to the periphery of the prosthesis, making it possible to suture or tack the peripheral edge of the patch to the abdominal wall, from within the pocket of the patch.

In one exemplary embodiment of the present invention, the second layer of the implantable prosthesis may contain at least one centrally located opening thus creating a peripheral rim of material against the first layer. The space or pocket between the rim and the first layer may be accessed through the hole so that the rim of material may be positioned and fixed to the muscle wall.

In accordance with another example embodiment of the present invention, the first layer of the implantable prosthesis may be, at least at portions of the peripheral edge, folded over, creating the second layer or rim or partial rim of material. The space between the rim or partial rim, and the first layer may be accessed so that the rim of material may be positioned and fixed to the muscle wall.

In accordance with yet another example embodiment of the present invention, the second layer of the prosthetic may contain a slit extending across at least a portion of the second layer, allowing access to the space between the first and second layers, so that the second layer of material may be positioned and fixed to the muscle wall.

In one embodiment, the implantable prosthesis may be at least in part constructed using a material that includes a plurality of interstices that are constructed and arranged to allow tissue in-growth into the abdominal wall. This material may include, but is not limited to polyethylene or polyester. This material may also be coated with an absorbable substance that reduces the formation of undesirable adhesions of tissue or organs to the implantable prosthesis.

In yet another embodiment, the implantable prosthesis is at least partially comprised of a biological material including but not limited to porcine, fetal porcine, bovine, fetal bovine, or equine dermis.

In one embodiment, at least a portion of the implantable prosthesis that faces and is placed against the muscle wall and muscle wall defect is susceptible to the formation of adhesions with tissue.

In accordance with further aspects of the present invention, the delivery device may consist of, but is not limited to polypropylene, polyethylene, silicone, nitinol or other types of plastic and/or metal materials.

In another embodiment, the delivery device has a generally planar support piece having an outer peripheral edge and an inner void spaced inwardly from the outer peripheral edge. The handle is secured to the delivery device adjacent to the void. The support piece contains a zone of weakness, preferably a slit or fold or region of increased flexibility, allowing the delivery device to be more easily folded or collapsed from its natural configuration, and fit into or removed from the implantable prosthesis.

Preferably, the zone of weakness extends from the outer periphery to the void, and preferably the zone of weakness is a radial slit.

A handle in the form of a tether(s), strap(s) or extension(s) can extend through the tissue or muscle wall defect when the implantable prosthesis and delivery device are positioned over the defect, for use in positioning the removable piece and the prosthesis, and for use in removing the prosthesis when properly positioned and fixed.

Preferably, the handle is secured to the support piece adjacent the void, and as a further preference, the handle is attached to the delivery device in a position that is diametrically opposite the zone of weakness in the support piece. Pulling on the handle, particularly in a direction that is obtuse to the direction of the slit, forces the delivery device against the mesh and/or muscle wall, urging the two sides of the slits to overlap each other, and urging the positioning device into a collapsed conformation. This urges the positioning device into its collapsed conformation and allows it to be readily removed from the implantable prosthesis and out of the muscle wall defect. The provision of the void has been found to reduce the forces required to maintain the support piece in a collapsed condition. Preferably, the handle has sufficient rigidity to impart a bending moment to the support piece to promote the folding of the support piece.

In a preferred embodiment, the handle is connected to the support piece along a radial line extending outwardly from the void toward the outer periphery and away from the zone of weakness. A spine is attached to overlie the handle and increase the localized stiffness of the support piece.

BRIEF DESCRIPTION OF THE DRAWINGS

Embodiments of the invention will now be described by way of example only with reference to the accompanying figures. These embodiments are further explained in the detailed description that follows.

DETAILED DESCRIPTION OF THE INVENTION

The present invention is a device that aids in the deployment, positioning and fixation of a prosthesis to an abdominal wall to repair a defect while limiting the amount of foreign body material implanted in the patient. Muscle wall defects can include, but are not limited to, umbilical hernias, epigastric hernias, incisional or other ventral hernias, inguinal hernias, femoral hernias, and muscle wall defects or holes left in the abdominal wall from trocars used for laparoscopic surgery. Described herein are only a few exemplary embodiments. One familiar with the art will recognize that parameters, including size and shape of the components of this invention, as well as the types of materials used for the components, may be altered to accommodate different types and/or sizes of abdominal wall defects while staying within the scope of the invention described herein.

Figure 3:
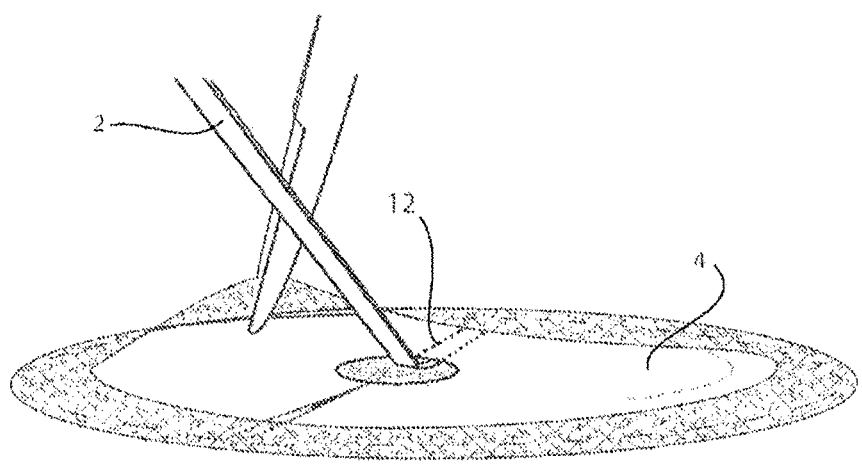
FIG. 3 illustrates in a top perspective view, the delivery device after it has been inserted into the prosthesis.

Referring firstly to FIG. 3, an implantable prosthesis P, consists of at least two juxtaposed layers, 7 and 8. Layers 7 and 8 are each constructed using a biologically compatible material. The material is flexible and includes a plurality of interstices that are arranged to allow tissue in-growth and integration into the abdominal wall. Suitable materials include polypropylene, polyester, polytetrafluoroethylene (PTFE) and expanded polytetrafluoroethylene (ePTFE). As a further preference the material used for the layers 7, 8, is knitted.

The second layer, 8, is formed as an annulus having an opening in the form of a centrally located hole, 9, which creates a peripheral rim of material when placed against the first layer, 7. Layers 7 and 8 are connected at the peripheral edge, such as by stitching, creating an enclosed accessible space or pocket, 11. In one example embodiment, the side of layer 7 that faces the patients' organs, shown in FIG. 4, as 7a, is covered in a substance that reduces the formation of undesirable adhesions of tissue or organs to the implantable prosthesis. One familiar with the art will recognize that this will be particularly important if the underlying layer, 7, is constructed from a knitted material or one that includes a plurality of interstices that could otherwise allow the formation of unwanted adhesions over time from the underlying organs or tissue.

In an alternative embodiment, layers 7 and 8 are constructed from biological material such as a collagen matrix, typically derived from human or animal tissue. Suitable materials include porcine, fetal porcine, bovine, fetal bovine, equine and human cadaver tissue.

Figure 1:
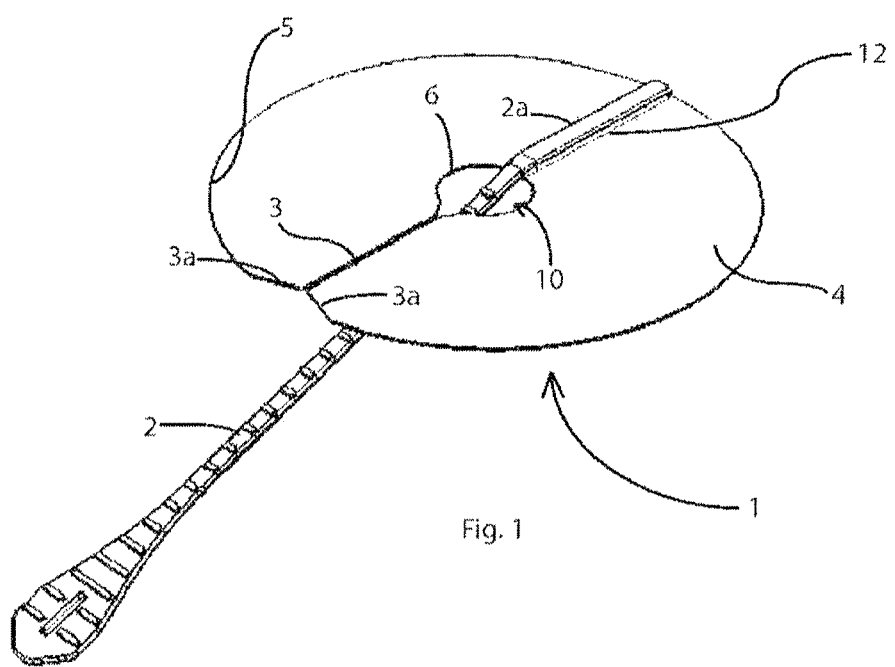
FIG. 1 depicts from a top perspective view, one exemplary embodiment of the delivery device.
Figure 2:
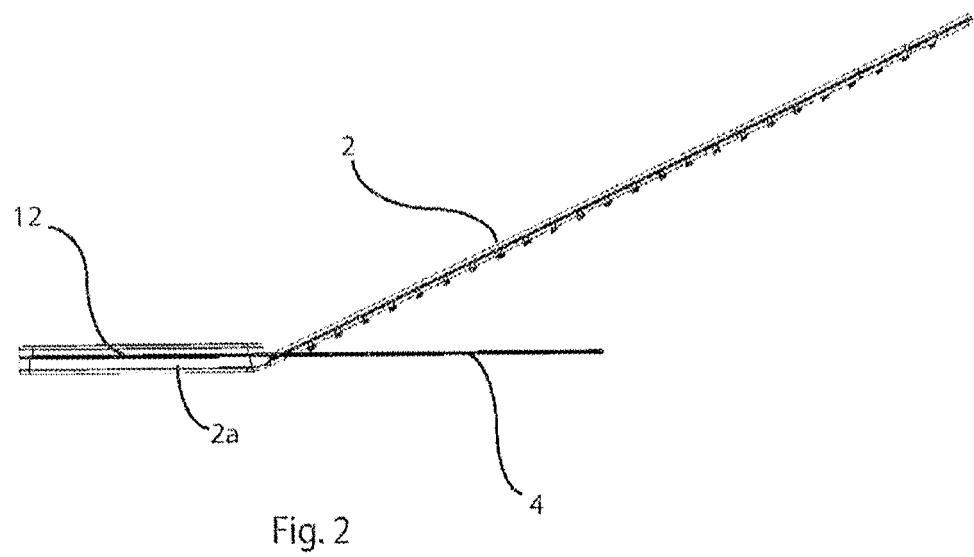
FIG. 2 is a section on the line II-II of FIG. 1.

Referring now to FIG. 1, a prosthesis delivery device 1, contains a planar support piece or platen, 4, and a handle, 2. The handle 2 is integrally formed with the platen 4 to inhibit separation of the handle 2 and platen, 4. The platen 4 is constructed out of biologically compatible flexible material such as an elastic plastic polymer material, typically one of polypropylene, polyethylene, polyethylene terephthalate, poly(glycolide-co-L-lactide), polydioxanone, and silicone, having flexibility sufficient to adopt a collapsed form allowing the support piece to pass through the opening, 9 of the prosthesis P.

The platen 4 has an outer peripheral edge 5 and a radially inner edge 6 defining a central void 10. In a typical application, the outer peripheral edge 5 and inner peripheral edge are both circular and so define an annulus. The platen 4 may be die cut from a sheet of material to define the edges 5, 6 and remove the material to provide void 10. Typically, the platen 4 will have a diameter slightly less than that of the pocket formed between the two layers 7, 8, of the prosthesis so as to fully support the prosthesis. The diameter of the platen 4 may vary between 3 cm and 40 cm.

The diameter of the void 10 is selected to maintain a substantially continuous surface over the extent of the layer 8 and in typical applications will have a diameter of between 0.2 cm. and 15 cm.

To facilitate flexure, the platen 4 has a zone of weakness, which, in the embodiment of FIG. 1, is a radial slit, 3, which extends from the inner edge 6 to the outer peripheral edge 5. The slit 3 allows the platen to more readily be folded from its natural or planar configuration, shown in FIG. 1, and into a conical collapsed configuration, shown in FIG. 3. In the planar configuration the edges of the slit 3 substantially abut to present on continuous planar surface and peripheral edge. The radial outer portions of the slit 3 are relieved, as shown at 3a, to facilitate sliding of the edges of the slit 3 in to a collapsed condition, as described below.

As shown in FIG. 1, the handle 2 is flexible but has sufficient rigidity to control movement of the platen and allow manipulation of the platen 4. In the embodiment of FIG. 1, the handle 2 is integrally formed with the platen 4 and extends 2 to 20 cm from the platen, but more preferably 5-15 cm from the platen. The handle 2 may be made from the same material as the platen 4, or from another material where different mechanical characteristics are required. Preferably, the material used for the handle 2 is polypropylene, polyethylene, nylon or polycarbonate, having a width that ranges from 0.5 mm to 20 mm, but more preferably 3-6 mm, and a thickness of 0.5 mm to 2.0 mm, but more preferable 0.7-1.2 mm, and having a flex modulus of 125,000 psi to 275,000 psi.

The handle 2 is secured to the platen 4 at the inner peripheral edge 6 and extends through the void 10 and along the opposite surface of the platen 4. The handle 2 is connected to the platen 4 diametrically opposite to the slit 3 and its terminal portion 2a extends radially along the platen 4 in a direction away from the slit 3. A reinforcing spine 12 is placed on the opposite side of the platen 4 to the handle 2, so as to be juxtaposed with the handle 2, and the spine 12 and handle 4 connected to the platen 4 by ultrasonic welding or other suitable technique.

To assemble the prosthesis P on the delivery device 1, the outer peripheral edge, 5, of the platen 4 is pushed downwardly to form a cone with the slit 3 accommodating the reconfiguration from the free body state. Once the platen 4 has been collapsed to a circumference less than that of opening 9, it may be positioned in the pocket 11 formed between the two layers 7, 8 of the prosthesis P. Once positioned, it may be released, allowing it to be restored into its natural planar orientation and nested between layers 7 and 8, as depicted in FIG. 3. With the platen 4 of the delivery device 1 nested between the layers 7, 8 of the prosthesis P, the delivery device 1 and the prosthesis P can be maneuvered and folded or flexed as a unit.

In order to provide complete coverage of the muscle wall defect, the surgeon will choose a prosthesis with an area that is larger than that of the muscle wall defect. In a repair known as an underlay repair, the prosthesis must be folded or rolled in order to fit it through the muscle wall, behind or posterior to the muscle wall defect. The delivery device 1 and the prosthesis P is packaged and presented to the user or surgeon, separately, or combined as seen in FIG. 3. In either case, it is important that the size of the platen 4 is large enough to fit between layers 7 and 8 without unintentionally or too easily sliding out from between layers and out of the centrally located hole, 9. It is also important that the platen 4 is not too large, and must be able to fit between layers 7 and 8, and within the pocket, 11, and within the boundaries created by the stitching, 10. The thickness, flexibility and/or elasticity of the platen 4 of the delivery device is selected to accommodate the different support requirements of varying sizes of prostheses P.

In one particular embodiment, the platen 4 is formed from a polymer such as polypropylene having a flex modulus from 125,000 to 175,000 psi. Amorphous PET has been found to be a suitable material. The thickness of the polymer used is generally between 0.05 mm to 2.0 mm, but is preferably between 0.1 mm and 1 mm. A thickness of 0.4 mm has been found suitable. The diameter of the removable piece will generally be 0.1 mm to 5.0 cm less than the internal diameter of the pocket 11. The diameter of the platen 4 will more specifically be 0.5 mm to 3.0 mm less than the diameter of the pocket 11.

Figure 4:
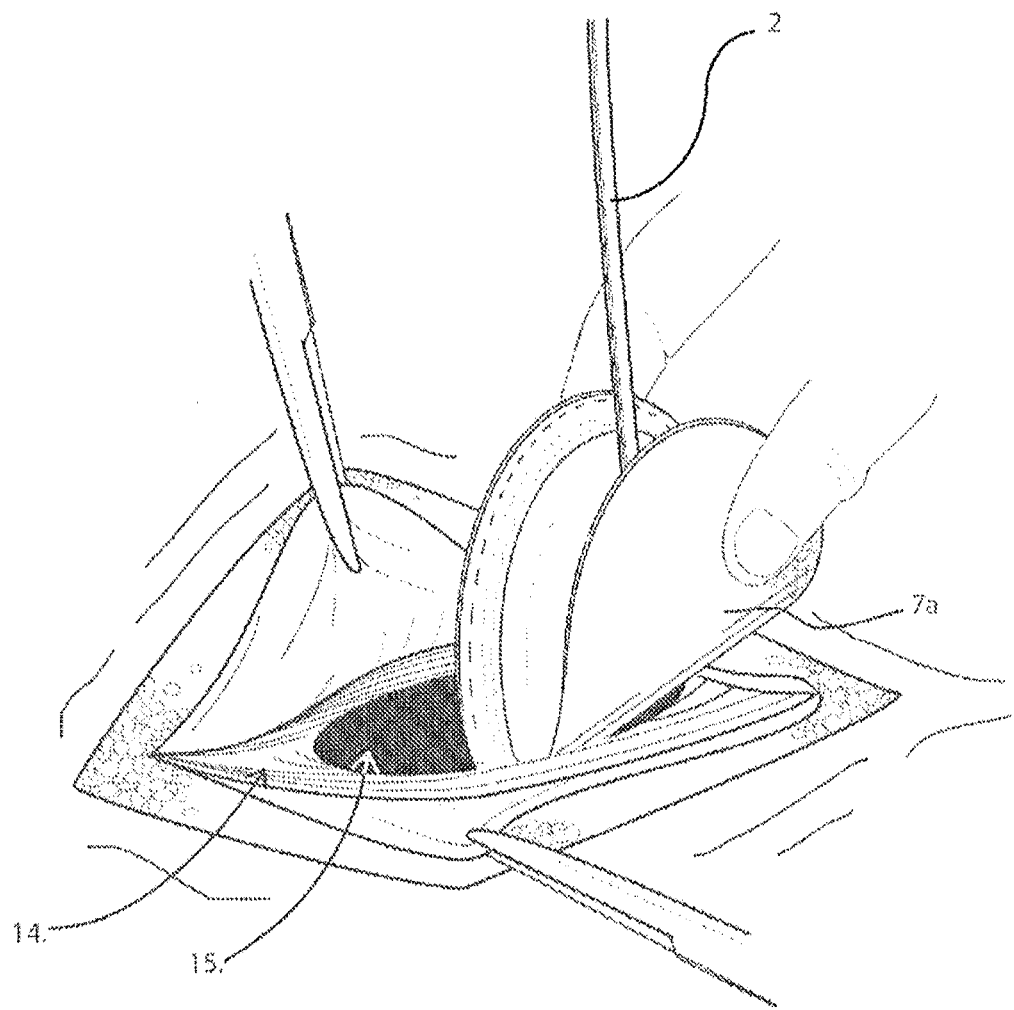
FIG. 4 illustrates in a top perspective view, the initial insertion of the delivery device through the muscle wall defect.

When combined, the platen 4 and the prosthesis P can be rolled or folded by the surgeon, for example in half as seen in FIG. 4, and inserted through the muscle wall defect, 15. Once on the posterior side of the abdominal wall, the surgeon can release the combined platen 4, and prosthesis P, allowing the platen 4 to return to its natural planar confirmation due to its elastic nature. The resilience of the platen 4 urges the prosthesis into the planar configuration as well, and provides a temporary support for the prosthesis P as it is positioned in place. This keeps the prosthesis, which is typically constructed from light-weight materials and can be flimsy, in an expanded, planar orientation relative to the abdominal wall. This makes it easier for the surgeon to fix the prosthesis to the posterior side of the abdominal wall surrounding the muscle wall defect, using for example, sutures or tacks.

Figure 5:
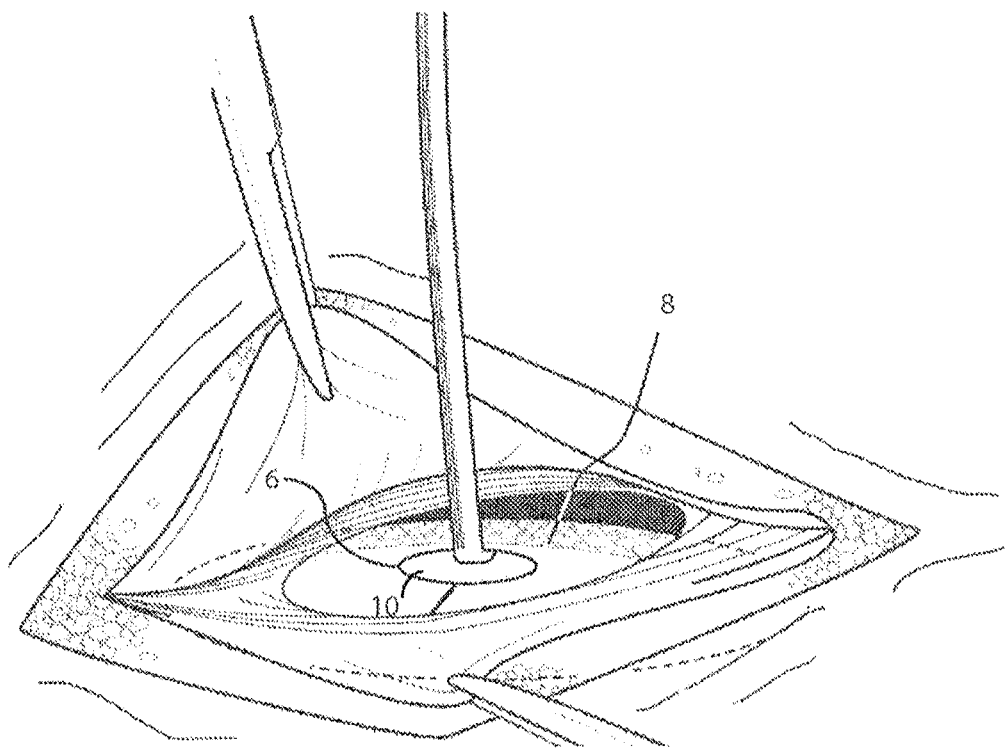
FIG. 5 illustrates in a top perspective view, the delivery device and prosthesis, after they have been inserted through the muscle wall defect.
Figure 6:
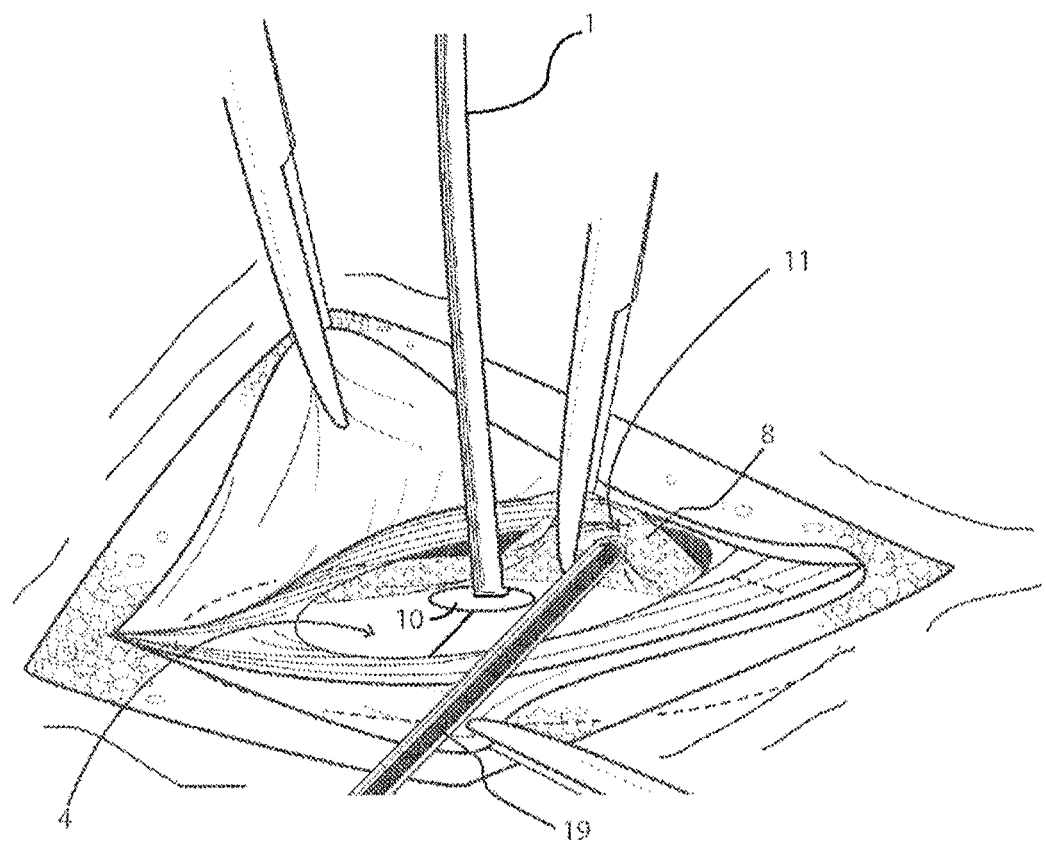
FIG. 6 illustrates in a top perspective view, the fixation of the prosthesis to the muscle wall.
Figure 7:
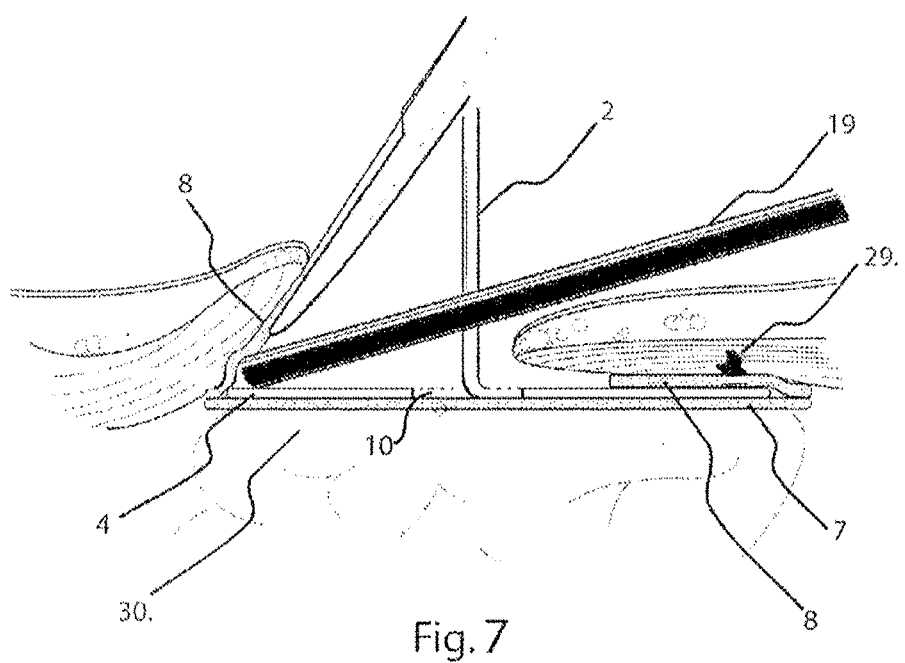
FIG. 7 illustrates in a cross-sectional view, on the line VII-VII of FIG. 6.

The handle 2 is configured to extend through the muscle wall defect so as to be accessible to the surgeon. The handle 2 is used by the surgeon to position and pull the platen 4 of the delivery device 1, along with the prosthesis, up against the muscle wall, as shown in FIG. 5, FIG. 6 and FIG. 7. Once the combined delivery device 1 and prosthesis P are in position relative to the muscle wall defect, the prosthesis is fixed to the underside or posterior side of the muscle wall defect. This may be done by using sutures or by using a tacker, 19 shown in FIG. 6 and FIG. 7. The end of the tacker 19 can, for example, be placed into the pocket 11 between the first and second layers of the prostheses, 7, 8, pushing the second layer of material, 8, upwards against the posterior side of the abdominal wall. A tack deployed from the end of the tacker, 19, can subsequently tack the second layer of material, 8, to the posterior side of the abdominal wall. FIG. 7 shows a tack, 29, that has been deployed, to pass through the second layer of material, 8, to the abdominal wall in this way. Subsequent tacks may be deployed in this fashion, along the entire peripheral edge of the prosthesis P until it is adequately anchored to the abdominal wall, and around the muscle wall defect. During this procedure, the handle 2 is used to ensure close contact between the layer of material 8 and the abdominal wall, whilst being flexible to allow adjustment for access of the tacker 19. Because the platen 4 of the delivery device, 1, lies below the tacker, 19, it deflects sutures or tacks that might otherwise unintentionally perforate underlying tissue and organs such as bowel, 30. Once the prosthesis 2 is fully anchored, tissue or organs should not be able to become lodged between the abdominal wall and the prosthesis.

The support provided by the platen 4 avoids the need for a separate support ring in the prosthesis and so allows the tacker 19 to access the prosthesis at the peripheral edge 5. One skilled in the art will recognize that it is important to access and fix the peripheral edge of the prosthesis to the posterior side of the abdominal wall to 1) ensure good apposition and integration of the prosthesis to the abdominal, and to 2) prevent tissue and organs lodging between the prosthesis and the abdominal wall to avoid dislodgment of the mesh and recurrence of the hernia or incomplete repair of the muscle wall defect.

Figure 8:
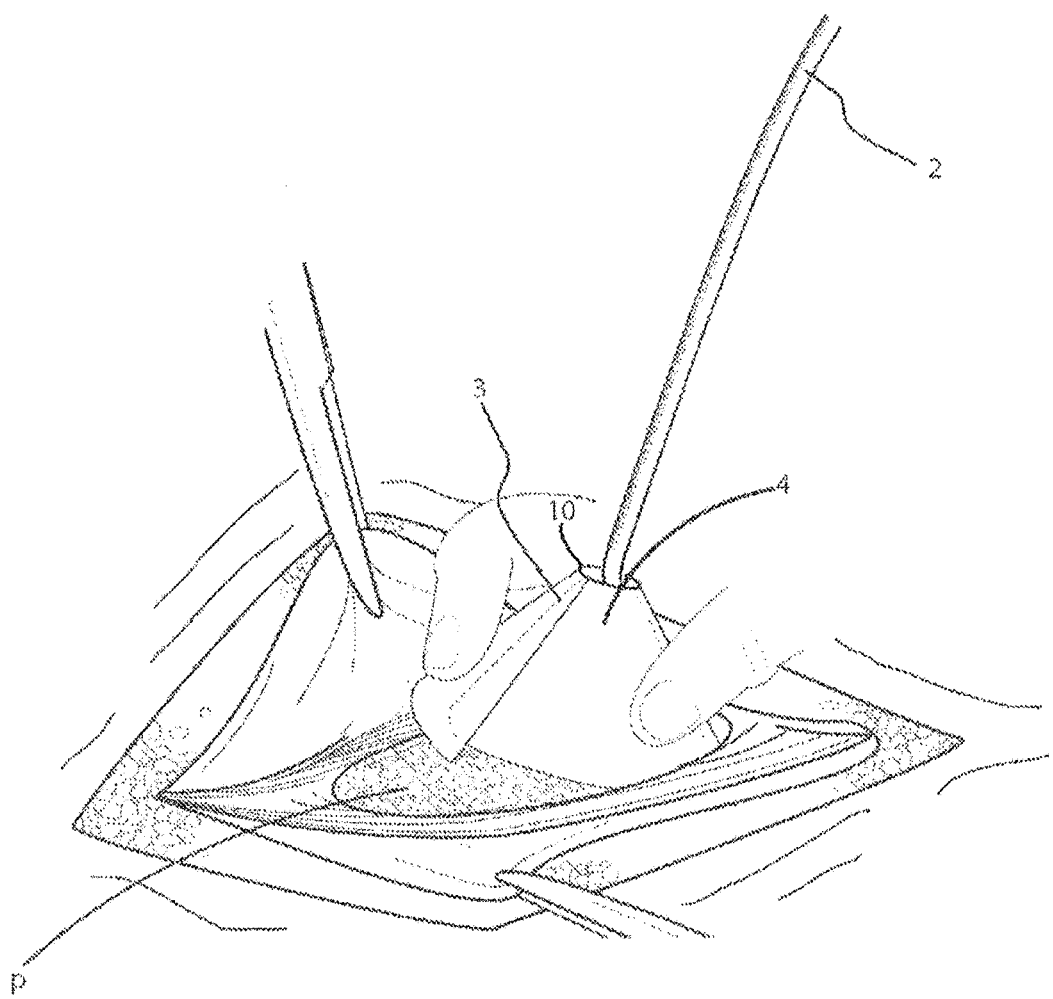
FIG. 8 illustrates in a top perspective view, the removal of the delivery device as it is removed from the prosthesis and retracted through the muscle wall defect.

After the prosthesis has been fixed to the muscle wall, the platen 4 can be removed from the pocket 11 of the prosthesis and retracted through the muscle wall defect by pulling on the handle 2, and forcing the platen, 4, into its collapsed position, as seen in FIG. 8. Anterior layers of tissue and skin are subsequently closed and sutured together.

The provision of the void 10 reduces the resistance of the platen 4 to move from its free body state in which the platen is planar and the edges of the slit 3 aligned, in to the collapsed position as shown in FIG. 8. The spine 12 also rigidifies the platen 4 locally to promote flexure of the platen 4 as the force is applied from the handle 2. The stiffness of the handle 2 enables a bending moment to be applied to the platen 4 so that the edges of the slit 3 will slide over one another and adopt a generally conical position. The relief provided by the terminal portions 3a assists in this initial movement.

Figure 9:
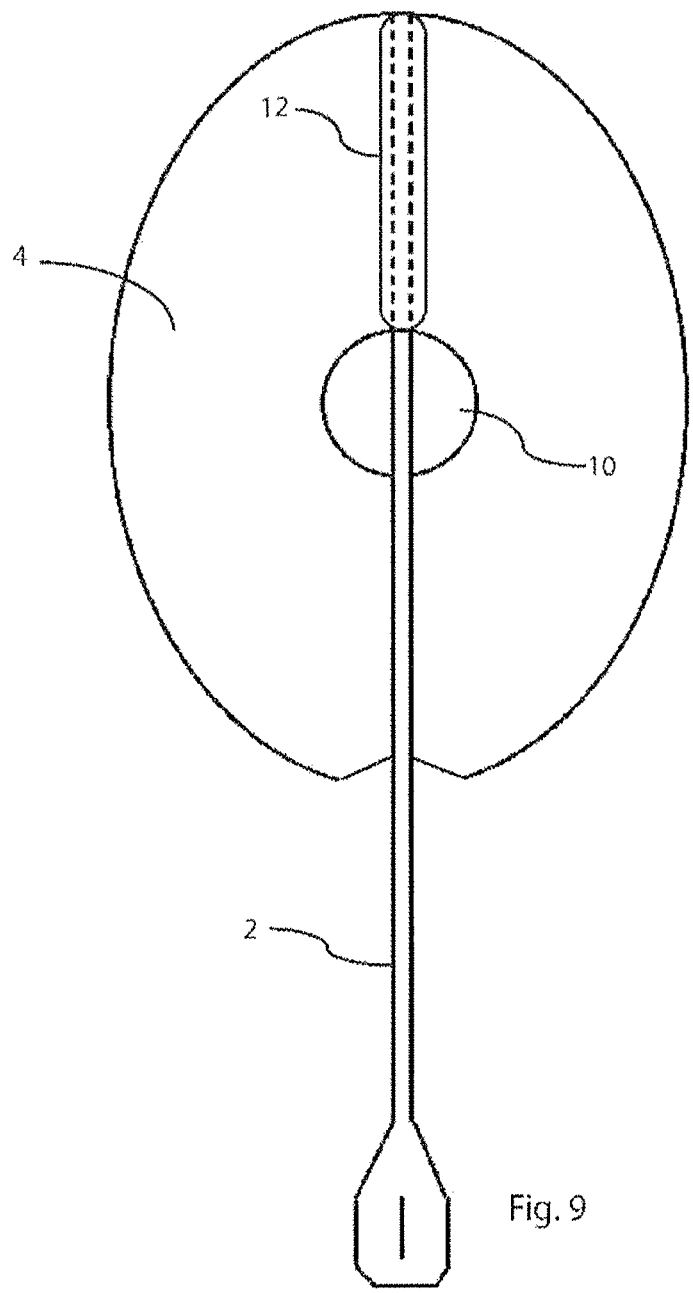
FIG. 9 is a plan view of a further embodiment of delivery device.

It will be apparent that the prosthesis may have configurations other than circular, and may for example be oval, as shown in FIG. 9. The void 10 may also be different shapes, but circular is preferred. The slit 3 in the platen 4 of the oval embodiment of FIG. 9 is positioned on a major axis of the oval and the attachment of the handle 2 is diametrically opposite the slit 3.

The invention claimed is:

1. A medical device for the repair of a muscle wall defect, comprising:
    a biologically compatible, implantable prosthesis having a first layer with a peripheral outer edge, said prosthesis having a flexibility sufficient to be transformed between an expanded shape and a reduced shape, said prosthesis having an interface to releasably engage said prosthesis with a delivery device; and
    a device for at least one of delivering or positioning said prosthesis relative to the muscle wall defect, said device having a support body with a flexibility sufficient to adopt a collapsed configuration for releasable engagement of said device to said interface, and with a flexibility sufficient to adopt a stable, self-supporting enlarged configuration to support said prosthesis in said expanded shape when said device is releasably engaged with said interface, said support body having a first side and an opposite second side, and a support opening passing through said support body between said first side and said second side, said device further comprising a handle having a free first portion extending through said support opening and extendable away from said first side of said support body and a second portion of said handle attached to said second side of said support body, said support body including a zone of weakness to facilitate adoption by said support body of said collapsed configuration, and a spine fixedly attached to said first side of said support body opposite said second portion.

2. The medical device recited in claim 1, wherein said interface includes a second layer juxtaposed with said first layer, said interface forming a pocket between said first layer and said second layer; one of said first layer and said second layer containing an interface opening to allow access to said pocket between said first layer and said second layer by said support body in said collapsed configuration.

3. The medical device according to claim 2, wherein said support body in said enlarged configuration is generally planar.

4. The medical device according to claim 3, wherein said zone of weakness allows at least one portion of said support body to overlap at least one other portion of said support body when said support body is in said collapsed configuration.

5. The medical device according to claim 2, wherein said handle is self-supporting and has sufficient rigidity to manipulate said support body to position said prosthesis relative to the defect.

6. The medical device according to claim 2, wherein said second layer of said prosthesis has an annulus shape.

7. The medical device according to claim 2, wherein said interface opening includes a slit extending across at least a portion of said second layer.

8. The medical device according to claim 2, wherein said first layer and said second layer are connected at said peripheral outer edge.

9. The medical device according to claim 2, wherein said support body has a substantially continuous surface between said support opening and an outer peripheral edge of said support body.

10. The medical device according to claim 2, wherein said second portion of said handle is attached to said second side of said support body adjacent said support opening.

11. The medical device according to claim 2, wherein said first layer at least in part includes a plurality of interstices to allow tissue in-growth.

12. The medical device according to claim 11, wherein said first layer is at least partially covered by a barrier that reduces the formation of adhesions of tissue or organs to said prosthesis.

13. The medical device according to claim 12, wherein said barrier includes a coating.

14. The medical device according to claim 2, wherein said zone of weakness includes a discontinuity extending between said opening and an outer peripheral edge of said support body.

15. The medical device according to claim 14, wherein said discontinuity is a radially extending slit.

16. The medical device according to claim 15, wherein said radially extending slit is linear.

17. The medical device according to claim 2, wherein said handle is attached to said support body at a location that is diametrically opposed to said zone of weakness in said support body.

18. The medical device according to claim 2, wherein said zone of weakness terminates at a portion of an outer peripheral edge of said support body, said portion of said outer peripheral edge in the form of a relief.

19. The medical device according to claim 1, wherein said spine is configured to locally rigidify said support body to promote flexure of said support body as a force is applied from said handle.

20. The medical device according to claim 1, wherein said second portion of said handle and said spine are juxtaposed opposite each other and extend in a radial direction from adjacent said support opening to adjacent an outer periphery thereof.

21. A device for at least one of delivering or positioning a biologically compatible, implantable prosthesis relative to a muscle wall defect, said device comprising:

a support body with a flexibility sufficient to adopt a collapsed configuration for releasable engagement of said device to the prosthesis, and with a flexibility sufficient to adopt a stable, self-supporting enlarged configuration to support the prosthesis in an expanded shape when said device is releasably engaged with the prosthesis, said support body having an outer periphery, a first side and an opposite second side, and an opening passing through said support body between said first side and said second side, said device further comprising a handle having a free, first portion extending through said opening and away from said first side of said support body and a second portion of said handle attached to said second side of said support body, said support body including a zone of weakness to facilitate adoption by said support body of said collapsed configuration, and a spine fixedly attached to said first side of said support body opposite said second portion.

22. The device according to claim 21, wherein said support body has oppositely directed continuous surfaces about a substantial portion of said outer periphery.

23. The device according to claim 21, wherein said zone of weakness is a discontinuity in a surface of said support body to permit adjacent portions of said support body to overlap.

24. The device according to claim 23, wherein said discontinuity is a radial slit.

25. The device according to claim 24, wherein said radial slit extends in a linear direction.

26. The device according to claim 21, wherein said handle is attached to said support body at a location that is diametrically opposed to said zone of weakness in said support body.

27. The device according to claim 21, wherein said support body is generally planar.

28. The device according to claim 21, wherein said spine is configured to locally rigidify said support body to promote flexure of said support body as a force is applied from said handle.

29. The device according to claim 21, wherein said second portion of said handle and said spine are juxtaposed opposite each other and extend in a radial direction from adjacent said opening to adjacent said outer periphery.

* * * * *